United States Patent
Wu et al.

(10) Patent No.: US 12,303,569 B2
(45) Date of Patent: *May 20, 2025

(54) LIPID NANOPARTICLE COMPOSITIONS AND USES THEREOF

(71) Applicant: CYTODIGM, INC., Natick, MA (US)

(72) Inventors: Bin Wu, Lexington, MA (US); Heliang Song, Natick, MA (US); Victoria Trantow, Natick, MA (US)

(73) Assignee: Cytodigm, Inc., Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/829,557

(22) Filed: Sep. 10, 2024

(65) Prior Publication Data

US 2025/0001003 A1    Jan. 2, 2025

Related U.S. Application Data

(63) Continuation of application No. PCT/US2023/026541, filed on Jun. 29, 2023.

(60) Provisional application No. 63/356,557, filed on Jun. 29, 2022.

(51) Int. Cl.

| | |
|---|---|
| *A61K 48/00* | (2006.01) |
| *A61K 9/51* | (2006.01) |
| *A61K 38/46* | (2006.01) |
| *C12N 15/113* | (2010.01) |
| *C12N 15/88* | (2006.01) |

(52) U.S. Cl.
CPC ........ *A61K 48/0033* (2013.01); *A61K 9/5123* (2013.01); *A61K 38/465* (2013.01); *C12N 15/113* (2013.01); *C12N 15/88* (2013.01); *C12N 2310/14* (2013.01)

(58) Field of Classification Search
CPC .............. A61K 48/0033; A61K 9/5123; A61K 38/465; C12N 15/113; C12N 2310/14
See application file for complete search history.

(56) References Cited

U.S. PATENT DOCUMENTS

| | | | |
|---|---|---|---|
| 2015/0291969 A1* | 10/2015 | Nair .................. | C12N 15/8216 |
| | | | 435/468 |
| 2021/0009718 A1 | 1/2021 | Ambrogelly et al. | |
| 2022/0142935 A1* | 5/2022 | Wu ..................... | A61K 9/5123 |

OTHER PUBLICATIONS

Gavin Nicoll et al., "Ganglioside GD3 expression on target cells can modulate NK cell cytotoxicity via siglec-7-dependent and- independent mechanisms" in Eur. J. Immunol. 2003. 33: 1642-1648. (Year: 2003).*
Tang, et al., "Durable protective efficiency provide by mRNA vaccines require robust immune memory to antigens and weak immune memory to lipid nanoparticles", Materials Today Bio, 25:100988, 2024, 17 pgs.
Tsakiri, et al., "Lipid-based nanoparticles and RNA as innovative neuro-therapeutics" Front. Pharmacol., 13:900610 (2022).

* cited by examiner

*Primary Examiner* — Blessing M Fubara
(74) *Attorney, Agent, or Firm* — Elmore Patent Law Group, P.C.; Carolyn S. Elmore; Jia Kang (57) ABSTRACT

The present invention provides a lipid nanoparticle (LNP) formulation comprising at least one sialic acid (SA)-containing lipid. The LNP formulation is capable of effectively binding cell surface Siglecs, transfecting certain cells in vitro and targeting certain cells in vivo. The present invention also provides methods of using the LNP compositions described herein for pharmaceutical applications. For example, the LNPs provided herein are useful for the intracellular delivery of a nucleic acid therapeutic to a subject.

17 Claims, 3 Drawing Sheets

LIPID NANOPARTICLE COMPOSITIONS AND USES THEREOF

RELATED APPLICATIONS

This application is a continuation of International Application No. PCT/US23/26541, which designated the United States and was filed on Jun. 29, 2023, published in English, which claims the benefit of U.S. Provisional Application No. 63/356,557, filed on Jun. 29, 2022. The entire teachings of the above applications are incorporated herein by reference.

BACKGROUND OF THE INVENTION

Nucleic acids such as DNA, mRNA, siRNA, and antisense oligonucleotide (ASO) have emerged as a new category of promising therapeutic agents to prevent and treat various diseases. However, there are still many unmet needs in translating nucleic acids into medicines. For example, delivering a nucleic acid cargo into target cells largely relies on viral vectors which lead to many safety and efficacy issues. In addition, safe, effective, and stable in vivo delivery of nucleic acid therapeutics remains a challenge. It is essential to incorporate the nucleic acids into formulations that can protect them from degradation and that allow cellular uptake and intracellular cargo release.

Lipid nanoparticles (LNPs) are promising vehicles to deliver nucleic acid therapeutics because LNP can effectively protect and transport nucleic acid cargos to cells. For example, Onpattro, an LNP-based siRNA drug, has been approved by the US FDA for the treatment of polyneuropathies induced by hereditary transthyretin amyloidosis. LNP-mRNA vaccines have now been in clinical use against COVID-19. These successes pave the way for clinical development of many other nucleic acid-based therapies enabled by LNP delivery.

An LNP formulation typically consists of the nucleic acid cargo and four main lipid components, i.e., a cationic or ionizable lipid, a neutral phospholipid, cholesterol, and a polyethylene-glycol (PEG)-lipid. The cationic or ionizable lipid interacts with the anionic nucleic acid during particle formation and facilitates the cell entry when administered. The phospholipid stabilizes the structure of the particle and, to some degree, modulates the biodistribution of the LNPs. Cholesterol modulates cell membrane integrity and rigidity and therefore further stabilizes the particles and increases the efficiency of the in vivo delivery.

PEG-lipid is also an important component of the LNP system. The PEG unit plays a key role in reducing the particle size and minimizing particle aggregation. For systemically administered LNPs, the PEG-lipid reduces clearance mediated by the kidneys and the mononuclear phagocyte system (MPS) and thus prolongs the blood circulation time so that the LNPs have enough time to reach their targeted site. In some cases, prolonged circulation can lead to improved disease targeting mediated by the enhanced permeability and retention (EPR) effect.

Although conventional lipid nanoparticles showed great success in delivering siRNAs and mRNAs, there are some drawbacks. For example, conventional LNPs have low efficiency in transfecting lymphocytes such as T cells and natural killer (NK) cells, as well as macrophages. T cells, NK cells, and macrophages are the targeted cells of many therapeutic modalities such as CAR-T, CAR-NK, and CAR-Macrophage therapies. Conventional LNPs also suffer from lack of in vivo targeting, especially the targeting of immune cells and tumor cells. It is also important to target immune cells and complement systems that are the sources of inflammation to treat inflammatory diseases. However, one may not be able to accomplish that using conventional LNPs.

In addition, LNPs administered systemically tend to predominately accumulate in the liver. As a result, most LNP-based therapies target liver and liver-related diseases. Therefore, "extrahepatic" delivery for the treatment of diseases that are non-liver related is a highly unmet needs in the biopharmaceutical field.

Recently, it has been reported that PEG-lipid in conventional LNP formulations may lead to the formation of anti-PEG antibody which can cause anaphylaxis, accelerated blood clearance (ABC), and unwanted immunogenicity. Therefore, it is desirable to replace PEG-lipid in the LNP formulations with a non-immunogenic entity.

These drawbacks limit the applications of LNPs in certain fields, e.g., adoptive cell therapy, in vivo cell engineering and gene therapy.

Sialic acid, also known as N-acetylneuraminic acid, is a nine-carbon sugar that binds to sialic acid-binding immunoglobulin-like lectin (Siglec). Sialic acid has mainly three derivatives, N-acetyl neuraminic acid (Neu5Ac), N-acetyl neuraminic acid hydroxyalkyl (Neu5Gc) and 3-deoxy-D-glycero-D-galacto-nonyl ketose (Kdn). There are other sialic acid derivatives that are further derived from these primary derivatives. One important sialic acid derivative is ganglioside, which is found in the brain and other human tissues.

Siglec, which is mostly expressed by various immune cells, has a predominantly intracellular immunoreceptor tyrosine-based inhibition motif (ITIM) that can mediate inhibitory signals upon binding to sialic acid and activate downstream inhibitory signaling through the recruitment of tyrosine phosphatases SHP-1 and SHP-2. There are several Siglecs that have intracellular immunoreceptor tyrosine-based activation motifs (ITAMs) that can mediate stimulatory signals upon binding to sialic acid and activate downstream stimulatory signaling. Sialic acid can also regulate the alternative pathway of complement activation. Major serum protein complement factor H recognizes sialic acid as a "self" marker, which helps to inhibit C1q/C3b fragment activation. In addition, sialic acid also binds a carbohydrate-binding lectin overexpressed in several types of cancers.

Aberrant interactions between sialic acid and Siglec are associated with a number of pathologies including infection, autoimmunity, inflammation and cancer. It can therefore be therapeutically beneficial to bind Siglecs on certain types of cells with a chemical or biological entity that comprises sialic acid residue to modulate the immune inhibition or activation for the treatment of pathologies including infection, autoimmunity, inflammation and cancer. Binding cell surface Siglecs also allow endocytosis and therefore be leveraged for cell targeting and intracellular delivery of therapeutic agents.

However, it is difficult to deliver such molecular entities of sialic acid to target cells in vivo. A common strategy is to attach the molecules of sialic acid or polysialic acid on the surface of nanoparticles so that the nanoparticles can carry the sialic acid entities to the cells of target.

Additionally, as sialic acid binds Siglecs on certain types of immune cells, chemical entities comprising sialic acid moiety can be attached on particles as ligands to guide said particles to the immune cells and cause the particles to bind the Siglecs on the cells. Such binding can facilitate the particles to enter the cell via receptor-mediated endocytosis. In this manner, nanoparticles loaded with therapeutic agents and surface-coated with sialic acid or sialic acid-containing entities can target immune cells and deliver therapeutic agents into the cells.

The conventional method for attaching sialic acid to the surface of lipid nanoparticles is by chemical conjugation. For example, a sialic acid molecule can be functionalized with a reactive group capable of forming a covalent bond with another reactive group on the nanoparticle surface. However, this method suffers from low conjugation efficiency and side reactions leading to undesired side-products in the pharmaceutical formulation.

Therefore, there is an unmet need for novel methods to attach ligands containing sialic acid to the surface of nanoparticles, especially LNPs to facilitate cell transfection and targeting via the binding of Siglecs by the SA-containing ligands on the LNPs.

SUMMARY OF THE INVENTION

The present invention in part provides a lipid nanoparticle (LNP) formulation comprising at least one sialic acid (SA)-containing lipid, said LNP formulation capable of effectively binding cell surface Siglecs, transfecting certain cells in vitro and targeting certain cells in vivo. The present invention also provides methods of using the LNP compositions described herein for pharmaceutical applications. For example, the LNPs provided herein are useful for the intracellular delivery of a nucleic acid therapeutic to a subject.

The SA-containing lipid can be synthetic or of natural origin and can comprise a plurality of sialic acid residues selected from the group consisting of Neu5Ac, Neu5Gc, and Kdn, or a combination thereof. The SA-containing lipid can have a molecular weight of from 200 to 500,000, from 500 to 100,000, and from 1,000 to 50,000 Da.

In some embodiments, the SA-containing lipid is formed by coupling a chemical entity comprising at least one SA unit with a fatty acid, wherein the fatty acid can be a saturated or non-saturated fatty acid, and can have 2-100, preferably 10-30, more preferably 13-21 carbons. In some embodiments, the SA-containing lipid can be linear and comprise only one lipid unit.

In some embodiments, the SA-containing lipid can be branched and comprise multiple lipid units.

In some embodiments, the SA-containing lipid is a naturally occurring lipid.

In some embodiments, the SA-containing lipid is a ganglioside, a ganglioside derivative, a mimetic, or a combination thereof.

Gangliosides are molecules composed of glycosphingolipids with one or more sialic acids linked on the sugar chain. Gangliosides can be synthetic or of natural origin.

The gangliosides used in the LNP compositions of the current invention may be a ganglioside containing one SA unit such as GM1, GM2, GM3, asialo-GM1, GA1, asialo-GM2, GA2, or two SA units such as GD1a, GD1b, GD2 and GD3, or three SA units such as GT1a, GT1b, GT1c, OAc-GT1b, GT3, or four SA units such as GQ1.

Other non-limiting examples of gangliosides include ganglioside-total, C18:0 (2-NBD) GM1, NGcGM3, C18:0 GM3, C20:0 GM1, C17:0 GM1 and C18:0 GM1; commercially available at Avanti Polar Lipids, Birmingham, AL.

For gangliosides that comprise only a single SA unit (such as in the case of GM1, GM2 and GM3), the SA may be linked with its neighboring sugar ring via an $\alpha 2,3$, $\alpha 2,6$, $\alpha 2,8$, or $\alpha 2,9$ linkage. For ganglioside that contains only one SA unit, an $\alpha 2,3$ linkage is preferred in the current invention.

The present invention also provides LNP formulations comprising at least one SA-containing lipid (such as a ganglioside) described herein, and methods of using the same. In addition to the nucleic acid cargo (such as a DNA, an mRNA or an siRNA), the LNP formulation may also contain other types of lipids including but not limited to a cationic lipid or an ionizable lipid, cholesterol, PEG-lipid and a phospholipid.

The cationic lipid is typically pharmaceutically acceptable and can be a natural or synthetic lipid. An example of a cationic lipid is an ammonium lipid, or lipid characterized by a positively charged nitrogen moiety. For example, the cationic lipid can be substituted by a tertiary ammonium group, such as a trialkyl ammonium, preferably a trimethyl ammonium. The cationic lipid can be further substituted by one or more substituted or unsubstituted long chain alkyls or alkenyls, such as a G4-C20 alkyl or alkenyl. Examples of commonly used lipids include multivalent cationic lipid, DOTMA, ethyl PC's, DDAB, pH sensitive lipids, diolcoyl-3-trimethylammonium propane (DOTAP), DC-cholesterol, and GL67.

An ionizable lipid is a class of lipid molecules that are neutral and non-ionic at physiological pH but will be protonated to become positively charged at lower pHs. Ionizable lipids can also form the complex with the SA-containing entity while promoting endosome escape and reducing toxicity. Examples of commercially available ionizable lipids include DLin-KC2-DMA, DLin-MC3-DMA, DLin-DMA, ALC-0315, SM-102, DODMA, and DODAP.

In order to increase the stability, functionality and other performance properties of the complex nanoparticles, other chemical entities commonly used in lipid nanoparticle (LNP) formulations such as structural lipids, PEGylated lipids, cholesterol, phospholipids, etc. may be added to the nanoparticle formulations of the present invention.

The invention provides a lipid nanoparticle composition comprising at least a ganglioside capable of binding cell surface Siglecs for the treatment of a disease or disorder, such as cancer, autoimmune and inflammatory diseases. The invention also comprises administering to the subject of the lipid nanoparticle composition.

The invention further provides for methods for delivering an active pharmaceutical ingredient (such as a nucleic acid)

to cells in a subject in need thereof. The invention comprises administering to the subject the composition.

The invention further relates to methods for the treatment of a disease or disorder, such as cancer or an autoimmune disease or an inflammatory disease, in a subject in need thereof comprising administering to the subject the composition of the invention.

The invention also relates to methods for the preparation of lipid nanoparticles capable of delivering a nucleic acid cargo into certain cells in vitro and targeting certain cells in vivo via systemic administration.

In addition, the invention also provides a lipid nanoparticle composition that does not comprise a PEG-lipid to reduce or eliminate the possibility of formation of anti-PEG, allergic reactions, accelerated blood clearance, and undesired immunogenicity.

BRIEF DESCRIPTION OF THE FIGURES

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
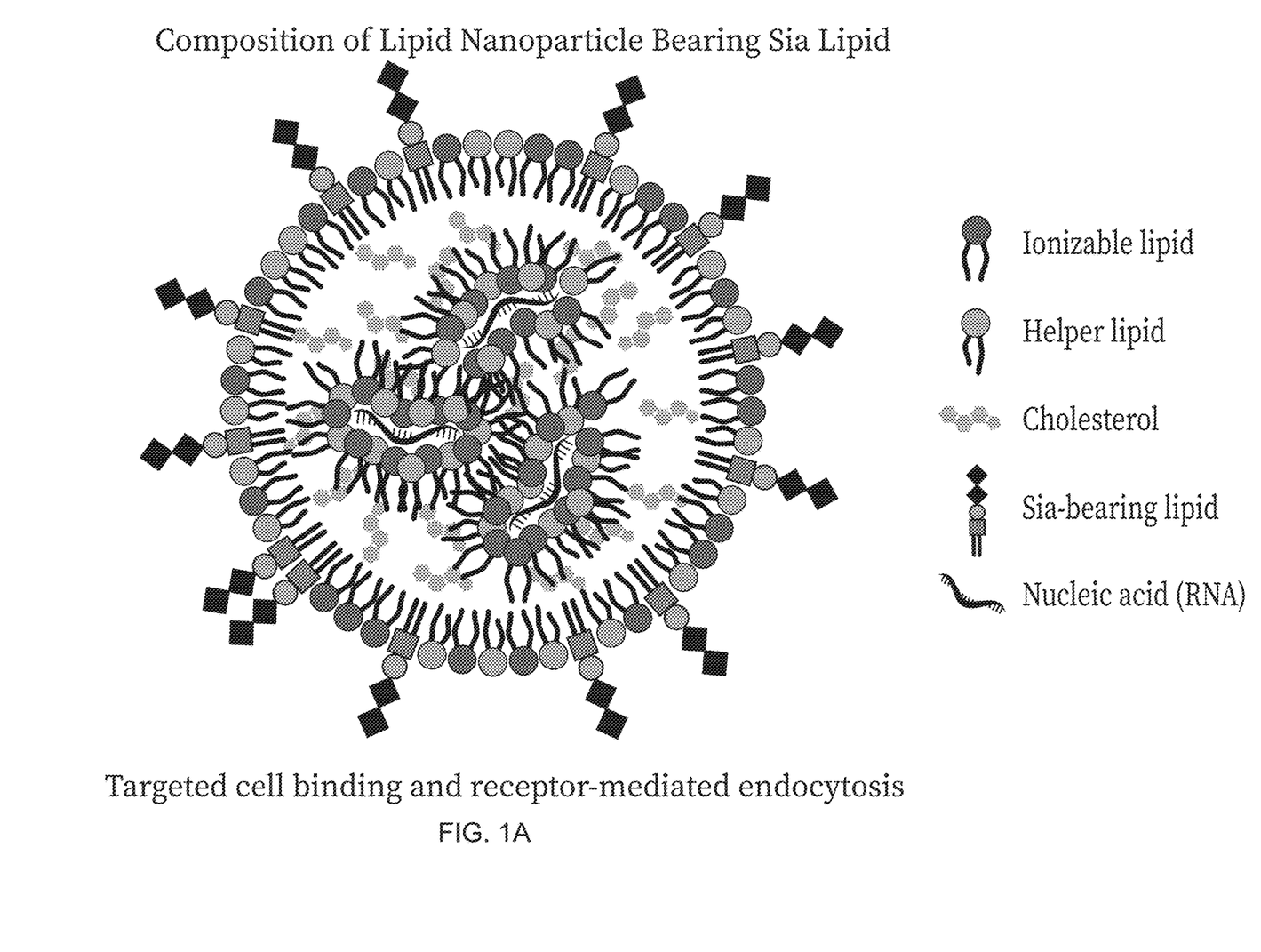
FIG. 1A is a cartoon of the LNP nanoparticle of the invention and FIG. 1B is a schematic of the LNP nanoparticle and its interaction with the target cell.
Figure 1B:
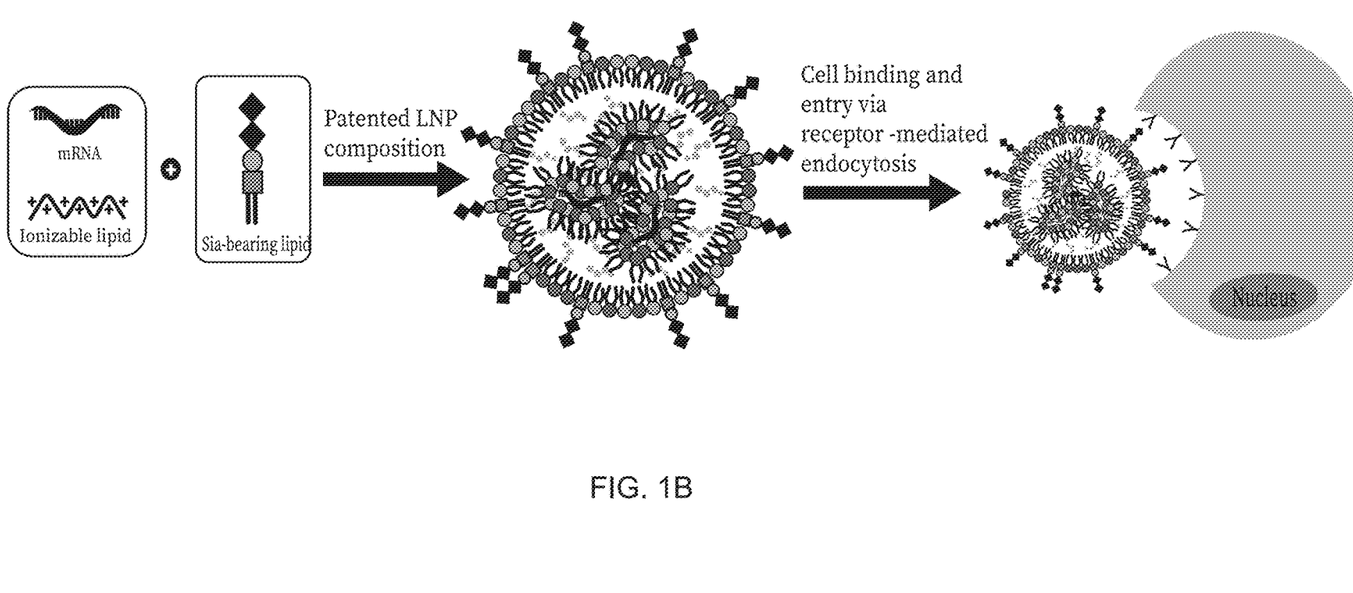
Figure 2A:
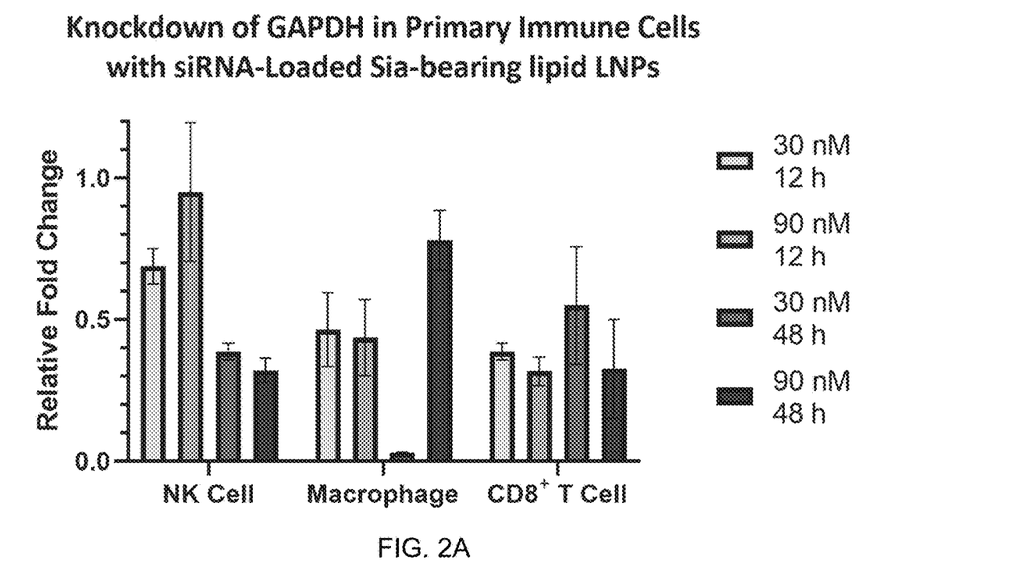
FIGS. 2A and 2B are graphs of GAPDH Knockdown in cells with SiRNA-loaded Sia-bearing lipid LNPs.
Figure 2B:
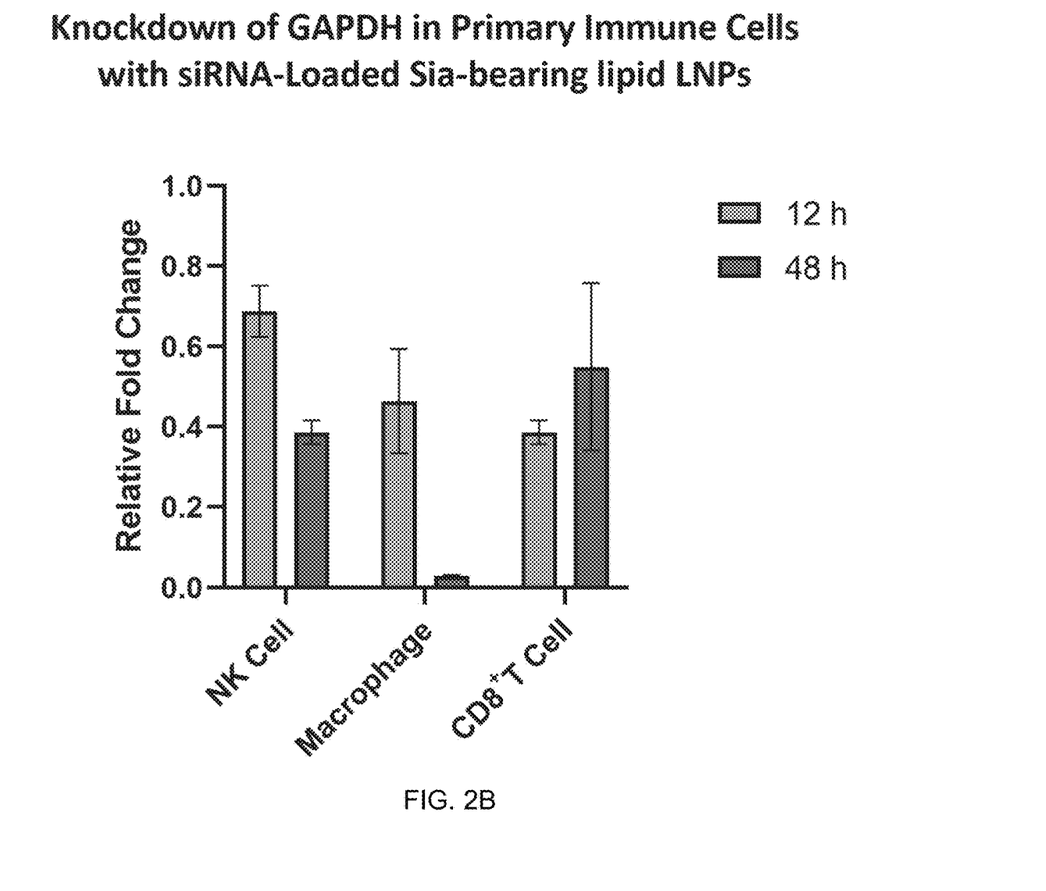

A description of preferred embodiments of the invention follows.

Definitions

As used herein, "pharmaceutically acceptable" includes those compounds, materials, compositions, and/or dosage forms which are, within the scope of sound medical judgment, suitable for medical or veterinary use when in contact with the tissues of human beings and animals at the concentration, dosage or amount present in the product, without causing excessive toxicity, irritation, allergic response, or other problems or complications, commensurate with a reasonable benefit/risk ratio. Preferably, a pharmaceutically acceptable material (e.g., polymer, excipient, surfactant, solvent, or microparticles/nanoparticles produced therefrom) is suitable or approved for human medical use.

As used herein, "nanoparticles" are preferably roughly round, sphere, or sphere-like in shape, and are generally within the size range of, e.g., between about 1-1,000 nm, between about 10-1,000 nm, or between about 50-1,000 nm, or between about 100-500 nm, as measured by dynamic light scattering, for example. The subject nanoparticles may also include particles that are less likely to clump in vivo.

Particle size and size distribution can be measured by a dynamic light scattering instrument, e.g., a Malvern Zetasizer. The particle size is typically reported as a Z-average diameter. Alternative techniques include, for example, sedimentation field flow fractionation, photon correlation spectroscopy, light scattering, light diffraction, and disk centrifugation. The term "nanoparticle" is not intended to convey any specific shape limitation. Such particles include, but are not limited to, those having a generally polyhedral or spherical geometry. Preferred particles are characterized by a spherical geometry typically produced by emulsion-based encapsulation processes. It is understood that the terms "microparticle" and "nanoparticle" are used interchangeably herein, unless accompanied by a specific description of size. For example, the term "microparticles" is intended to also embrace "nanoparticles" as if stated as "microparticles and/or nanoparticles" unless the context demands otherwise.

It is not necessary that each nanoparticle be uniform in size, although they are generally of a size sufficient to trigger endocytosis in an antigen presenting cell (APC), other MPS cell, or lymphocyte. Preferably, the subject nanoparticles have a diameter sufficient to trigger phagocytosis in an antigen presenting cell (APC), macrophages, NK cells, T cells, and/or other MPS cell.

The term "particle" encompasses both nanoparticle and microparticles.

As used herein "a" or "an" means one or more unless otherwise specified.

As used herein, "about" generally means up to ±10% of the particular term being modified.

The terms "sialic acid residue" and "sialic acid moiety" as well as their plural referents, and the like, are used interchangeably herein.

As used herein, the term "subject" is used to mean an animal, preferably a mammal, including a human or non-human. The terms "patient" and "subject" may be used herein interchangeably.

"Treatment" or "therapy" of a subject refers to any type of intervention or process performed on, or the administration of an active agent to, the subject with the objective of reversing, alleviating, ameliorating, inhibiting, slowing own or preventing the onset, progression, development, severity or recurrence of a symptom, complication, condition or biochemical indicia associated with a disease. As used herein, "treatment" (and grammatical variations thereof such as "treat" or "treating") includes to clinical intervention to alter the natural course of a disease in the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, combinations of the invention are used to delay development of a disease or to slow the progression of a disease.

Ganglioside

Gangliosides are molecules composed of glycosphingolipid with one or more sialic acids linked on the sugar chain. They form lipid rafts in the outer leaflet of the cell plasma membrane, especially in neuronal cells in the central nervous system. Gangliosides have been found to be highly important molecules in immunology as they participate in cellular proliferation, differentiation, adhesion, signal transduction, cell-to-cell interactions, tumorigenesis and metastasis. More than 60 gangliosides are known.

Ganglioside GM1

Ganglioside GD3 Disodium Salt

Gangliosides can be named based on the number of SA unit they have in the molecule. Thus, gangliosides having one SA unit are named as "GM" such as GM1, GM2 and GM3. Here, "G" stands for "ganglioside" and "M" stands for "mono." Similarly, "GD", "GT" and "GQ" would refer to gangliosides having two ("di"), three ("tri"), and four ("quadruple"), respectively. As an illustration, the structures of gangliosides GM1 and GD3 are shown above.

The SA unit in the ganglioside molecules can bind Siglecs expressed on various types of cells including immune cells and tumor cells. Thus, lipid nanoparticles incorporating a ganglioside molecule on the nanoparticle surface may facilitate the binding of Siglecs for disease treatment, and the delivery of nucleic acid cargo into cells via receptor-mediated endocytosis.

In one specific embodiment of the present invention, gangliosides having SA units and α2,8 linkages may bind Siglec-7 expressed on natural killer (NK) cells and can thus be incorporated in a specific lipid nanoparticle formulation to facilitate the delivery of a nucleic acid cargo into NK cells. Non-limiting examples of such gangliosides include GM2b, GD3, GT1a, GT3, and GQ1b.

In another embodiment, lipid nanoparticle incorporating other gangliosides can be used to target other immune cells such as monocytes, macrophages, dendritic cells, B cells, neutrophils, T cells, etc.

In addition, since sialic acid also binds several receptors on tumor cells, ganglioside-containing LNPs can be leveraged to target tumor site via the high-avidity binding of sialic acid to lectins.

The gangliosides can be added to the formulation in an amount of at least about 0.1% (molar percentage total lipid in the composition) (including any PEG-lipid that may be added as explained in more detail below), preferably between 0.1-50%, 0.5-20%, or 1-10%. The ganglioside preferably has 1, 2, 3, 4 or more sialic acid units.

Cationic and Ionizable Lipid

Thus, a lipid may have a positive or partial positive charge at physiological pH. Such lipids may be referred to as cationic or ionizable (amino) lipids. Lipids may also be zwitterionic, i.e., neutral molecules having both a positive and a negative charge.

In some embodiments, the lipid can be selected from, for example Dioleoyl-3-trimethylammonium propane (DO-TAP), 1,2-di-O-octadecenyl-3-trimethylammonium propane (DOTMA), 3-(didodecylamino)-N1,N1,4-tridodecyl-1-piperazineethanamine (KL10), N1-[2-(didodecylamino)ethyl]-N1,N4,N4-tridodecyl-1,4-piperazinediethanami-ne (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3.beta.)-cholest-5-en-3-yloxy]octyl}oxy)-N,N-dimethyl-3-[(9Z, 12Z)-octadeca-9,12-dien-1-yl oxy]propan-1-amine (Octyl-CLinDMA), (2R)-2-({8-[(3.beta.)-cholest-5-en-3-yloxy] octyl})oxy)-N,N-dimethyl-3-[(9-Z, 12Z)-octadeca-9,12-dien-1-yloxy]propan-1-amine (Octyl-CLinDMA (2R)), and (2S)-2-({8-[(3.beta.)-cholest-5-en-3-yloxy]octyl}oxy)-N,N-dimethyl-3-[(9Z-,12Z)-octadeca-9,12-dien-1-yloxy]propan-1-amine (Octyl-CLinDMA (2S)).

An ionizable lipid is a class of lipid molecules that are neutral and non-ionic at physiological pH but will be protonated to become positively charged at lower pHs. Ionizable lipids can also form the complex with the SA-containing entity while promoting endosome escape and reducing toxicity. Examples of commercially available ionizable lipids include DLin-KC2-DMA, DLin-MC3-DMA, DLin-DMA, DODMA, DODAP, ALC-0315, SM-102, SS-OP, SS-EC, etc.

The cationic lipid can be added to the formulation in an amount of at least about 10% (molar percentage total lipid in the composition) (including any PEG-lipid that may be added as explained in more detail below), preferably at least 20%, at least 30%, at least 40%, at least 41%, at least 42%, at least 43%, at least 44%, at least 45%, at least 46%, at least 47%, at least 48% or at least 49%. For example, the cationic lipid can be present in an amount between 25 and 75% (molar percentage total lipid), preferably between 30 and 60%, more preferably between 45 and 55%.

PEG Lipid

Polyethylene Glycol (PEG) lipids can also be used. The term "PEG lipid" refers to polyethylene glycol (PEG)-modified lipids. Non-limiting examples of PEG lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. In some embodiments, a PEG lipid can be PEG-c-DOMG, PEG-DMG, PEG-DLPE, PEG-DMPE, PEG-DPPC, or a PEG-DSPE lipid.

The PEG-lipid can be added to the formulation in an amount of at least about 1% (molar percentage total lipid in the composition) (including any PEG-lipid that may be added as explained in more detail below), of at least about 0.1% (molar percentage total lipid in the composition) (including any PEG-lipid that may be added as explained in more detail below), preferably between 0.1-50%, 0.5-20%, or 1-10%.

It is to be noted that in the current invention, the addition of PEG-lipid is optional. It is beneficial to construct the LNPs without a PEG-lipid as PEG-lipid may lead to the formation of anti-PEG, which may cause anaphylaxis, accelerated blood clearance, and unwanted immunogenicity. The ganglioside in the LNPs of the current invention can act to stabilize the nanoparticles and prolong the circulation time of the LNPs in the blood circulation to allow the nanoparticles to find their targeted site. Without being bound by any theory, it is believed that the ganglioside resides on the surface of the LNP to create a hydrophilic particle surface, thus avoiding being taken up by the MPS and prolonging the circulation.

The hydrophilic nature of the LNPs of the current invention may also reduce the formation of protein coronas such as the ones formed by apolipoproteins, e.g., Apo-E. Apo-E corona has been believed to drive the nanoparticles to the liver. Therefore, the LNP compositions of the current invention may also be utilized for the delivery of therapeutic agents to tissues and organs other than the liver. Such "extrahepatic" organs include but are not limited to spleen, kidney, lung, heart, bone marrow, lymph nodes, brain, skin, ear, and eye.

In order to increase the stability, functionality and other performance properties of the LNP formulations, other chemical entities commonly used in lipid nanoparticle (LNP) formulations such as structural lipids, cholesterol, phospholipids, etc. may be added to the nanoparticle formulations of the present invention.

For example, cholesterol can be present in an amount between 5 and 60% (molar percentage total lipid), preferably between 10 and 55%, more preferably between 25 and 50%.

Phospholipids include distearoylphosphatidylcholine (DSPC), diolcoylphosphatidylcholine (DOPC), dipalmitoylphosphatidylcholine (DPPC), dioleoyl-phosphatidylethanolamine (DOPE), palmitoylolcoylphosphatidylcholine (POPC), palmitoyloleoyl-phosphatidylethanolamine (POPE) and dioleoyl-phosphatidylethanolamine 4-(N-malcimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-diclaidoyl-sn-glycero-3-phophocthanolamine (trans DOPE). In one preferred embodiment, the phospholipid is distearoylphosphatidylcholine (DSPC). The phospholipid can be present in an amount between 1 and 50% (molar percentage total lipid), preferably between 2 and 40%, more preferably between 5 and 15%.

Active Agent

The LNPs described can further comprise an active agent. The composition can comprise an API. The API can be encapsulated within the LNP. The amount of the API can be about 0.01 to about 50% (w/w) of the nanoparticle, or about 0.05 to about 25%, about 0.1 to about 10%, about 0.2 to about 5%, about 0.5 to about 3%, about 1 to about 5%, or about 2 to about 5% (w/w) of the nanoparticle. The ratio of lipids to nucleic acid can be about 1 to 20, preferably 3 to 15, more preferably 5 to 10.

In certain aspects, the active agent is advantageously a drug (also referred to herein as an active pharmaceutical ingredient, or API). However, active agents that are non-therapeutic can also be included as part of the particles according to the methods. For example, agents useful in diagnostics, agriculture, cosmetics, personal products, home products, industrial chemicals, dyes, fluorescing agents or coloring agents and the like can be included. Preferred active ingredients are oligonucleotides, nucleic acid molecules and mimics thereof, such as DNA, RNA, PNA, siRNA, microRNA, ORNA, antisense, oligonucleotide, aptamer, and a combination thereof. It is understood that an API can be substituted with non-therapeutic compounds, such as diagnostic, agricultural, or chemical agents. Therefore, in each instance where the term API is used, it shall be understood that the term "active agent," including diagnostic, agricultural or chemical agents can be used in lieu thereof. The term "API" and "cargo" are used interchangeably herein.

Production of the Particles

The LNPs can be manufactured from the coprecipitation of the lipids and the nucleic acid. In general, the SA-containing lipid (such as a ganglioside) can be dissolved along with other lipids in a preferably water-miscible organic solvent, such as an alcohol. Any nucleic acid API can be dissolved in the aqueous medium or organic solvent. The two solutions are then combined. Preferably, the aqueous solution and organic solution are combined slowly (e.g., dropwise) or with mixing (e.g., via a microfluidic device) to incur nanoprecipitation. For example, a small amount of organic solution can be added to the aqueous phase with mixing.

The particles may also be manufactured using a pre-assembled device such as a T-mixer, or an automated, microfluidic device such as NanoAssemblr of Precision Nanosystems and Automated Nanoparticle System of Particle Works.

Exemplary solvents miscible with water include methanol, ethanol, acetone, tetrahydrofuran (THF), acetonitrile, dimethyl sulfoxide (DMSO), and dimethylformamide (DMF).

Solvent is then removed and/or particles collected, for example, by evaporation, solvent exchange, centrifugation or filtration, dialysis, tangential flow filtration, followed by dehydration, e.g., concentration or lyophilization.

The aqueous solution can optionally comprise a surfactant comprising organic or inorganic pharmaceutical excipients; various polymers; oligomers; natural products; nonionic, cationic, zwitterionic, or ionic surfactants; and mixtures thereof. The surfactant may comprise an acidic buffer such as citrate, polyvinyl alcohol (PVA), polyvinylpyrrolidone (PVP), a polysorbate (Tween series) surfactant, a PEO-PPO-PEO (polyethylene oxide-polypropylene oxide-polyethylene oxide) triblock copolymer (Pluronic series or Poloxamer series) surfactant, or a t-octylphenyl-polyethylene glycol (Triton X-100) surfactant or a salt, derivative, copolymer, or mixture thereof.

Particle Sizes

The size of the subject nanoparticles is from about 1 nm to about 10 μm, preferably from about 10 nm to about 2 μm, and more preferably from about 20 nm to about 1 μm, and most preferably from about 40 nm to about 500 nm. For example, the nanoparticles may have an average size between about 50 and 900 nm, such as about 50, 75, 100, 300, 500, 700, or 900 nm.

As used herein, particle size can be determined by any conventional particle size measuring techniques well known to those skilled in the art. Such techniques include, for example, sedimentation field flow fractionation, photon correlation spectroscopy, light scattering, dynamic light scattering, light diffraction, and disk centrifugation.

Pharmaceutical Composition

One aspect of the present invention provides pharmaceutical compositions which comprise the subject lipid nanoparticles, and optionally comprise a pharmaceutically acceptable carrier or excipient. Preferably, these compositions optionally further comprise one or more additional therapeutic agents. Alternatively, the subject particles of the current invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, an immunotherapeutic agent, or a chemotherapeutic agent, or it may be any one of a number of agents undergoing approval in the Food and Drug Administration. It will also be appreciated that certain of the subject particles of present invention can exist in free form for treatment, or where appropriate, as a pharmaceutically acceptable derivative thereof.

Preferably, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants, adjuvants including but not limited to Alum, MF59, AS04, and CPG can also be present in the composition, according to the judgment of the formulator.

In certain embodiments, the subject is a human patient. In certain embodiments, the subject is a non-human mammal, such as a non-human primate, a livestock animal (horse, mule, cattle, bull, cow, sheep, goat, pig, camel, etc.), a rodent (rabbit, hamster, mouse, rat, etc.), or a pet (cat, dog).

In one embodiment, the method includes administering the subject composition or pharmaceutical composition comprising the subject microparticles or nanoparticles (e.g., the carboxylated particles) by any suitable means or routes, such as orally, nasally, intravenously, intramuscularly, ocularly, transdermally, or subcutaneously. In a particular embodiment, the particles are administered nasally. In still another embodiment, the particles are administered intravenously.

EXAMPLES

Example 1. Preparation of Lipid Nanoparticles Comprising Poly(A) and Ganglioside GM3

Ganglioside GM3 was dissolved in a mix of solvents consisting of 1 part of ethanol and 3 parts of methanol. Other lipids were dissolved in ethanol. MC3, Cholesterol, DSPC, and GM3 were mixed with a molar ratio of 50:38.5:10:1.5. Poly(A) (MW 700,000-3,500,000, chain length 2,100-10,000 nucleotides) was dissolved in 10 mM citrate buffer (pH 3). The volume of the citrate buffer was 7.5 ml, and the volume of the lipid solution was 2.5 ml. The two solutions were loaded into two syringes which were mounted on a syringe pump, and were subsequently introduced to a T-mixer at a flow rate of 8 ml/min for the lipid solution and 24 ml/min for the Poly(A) solution to achieve an N:P ratio of 5.79. The resulting lipid nanoparticles were found to have a Z-average particle size of 93.7 nm and a zeta potential of −11.9 mV.

Example 2. Preparation of Lipid Nanoparticles Comprising Poly(A) and Ganglioside GM3

Ganglioside GM3 was dissolved in a mix of solvents consisting of 1 part of ethanol and 3 parts of methanol. Other lipids were dissolved in ethanol. MC3, Cholesterol, DSPC, and GM3 were mixed with a molar ratio of 48.5:37.3:9.7:4.5. Poly(A) (MW 700,000-3,500,000, chain length 2,100-10,000 nucleotides) was dissolved in 10 mM citrate buffer (pH 3). The volume of the citrate buffer was 7.5 ml and the volume of the lipid solution was 2.5 ml. The two solutions were loaded into two syringes which were mounted on a syringe pump, and were subsequently introduced to a T-mixer at a flow rate of 8 ml/min for the lipid solution and 24 ml/min for the Poly(A) solution to achieve an N:P ratio of 5.79. The resulting lipid nanoparticles were found to have a Z-average particle size of 122.3 nm and a zeta potential of −14.6 mV.

Example 3. Preparation of Lipid Nanoparticles Comprising Poly(A), PEG-Lipid and Ganglioside GM3

Ganglioside GM3 was dissolved in a mix of solvents consisting of 1 part of ethanol and 3 parts of methanol. Other lipids were dissolved in ethanol. MC3, Cholesterol, DSPC, DMG-PEG2000, and GM3 were mixed with a molar ratio of 49.2:37.9:9.8:1.5:1.5. Poly(A) (MW 700,000-3,500,000, chain length 2,100-10,000 nucleotides) was dissolved in 10 mM citrate buffer (pH 3) with an N:P ratio of 5.79. The volume of the citrate buffer was 7.5 ml and the volume of the lipid solution was 2.5 ml. The two solutions were loaded into two syringes which were mounted on a syringe pump and were subsequently introduced to a T-mixer at a flow rate of 8 ml/min for the lipid solution and 24 ml/min for the Poly(A) solution to achieve an N:P ratio of 5.79. Next, the LNP was dialyzed against PBS for 12 hours. The resulting lipid nanoparticles were found to have a Z-average particle size of 65.7 nm and a zeta potential of −2.54 mV.

Example 4. Preparation of Lipid Nanoparticles Comprising Poly(A), PEG-Lipid and Ganglioside GD3

Ganglioside GD3 is dissolved in a mix of solvents consisting of 1 part of water and 3 parts of ethanol. Other lipids are dissolved in ethanol. MC3, Cholesterol, DSPC, DMG-PEG2000, and GD3 were mixed with a molar ratio of 49.2:37.9:9.8:1.5:1.5. Poly(A) (MW 700,000-3,500,000, chain length 2,100-10,000 nucleotides) is dissolved in 10 mM citrate buffer (pH 3). The two solutions are introduced to a T-mixer, and the resulting LNPs are dialyzed against PBS for 12 hours.

Example 5. Preparation of Lipid Nanoparticles Comprising mRNA, PEG-Lipid and Ganglioside GD3

Ganglioside GD3 is dissolved in a mix of solvents consisting of 1 part of water and 3 parts of ethanol. Other lipids are dissolved in ethanol. MC3, Cholesterol, DSPC, DMG-PEG2000, and GD3 are mixed with an appropriate molar ratio. A GFP mRNA is dissolved in an aqueous buffer. The two solutions are introduced to a T-mixer, and the resulting LNPs are dialyzed against PBS for 12 hours.

Example 6. Preparation of Lipid Nanoparticles Comprising siRNA, Ionizable Lipid MC3, Cholesterol, Phospholipid, PEG-Lipid and 3 Mol % Ganglioside GD3

Ganglioside GD3 was dissolved in methanol. All other lipids were dissolved in ethanol. MC3, Cholesterol, DSPC, PEG2000, and GD3 were mixed with a molar ratio of 49:37.5:9:1.5:3. A Silencer™ GAPDH siRNA (ThermoFisher) was dissolved in 10 mM citrate buffer (pH 3). The volume of the citrate buffer was 3.0 ml, and the volume of the lipid solution was 1.0 ml. The two solutions were loaded into 5 mL Luer-lok syringes which were mounted on a syringe pump, and subsequently introduced to a T-mixer at a flow rate of 5 ml/min for the lipid solution and 15 ml/min for the RNA solution to achieve an N:P ratio of 6:1. After mixing, the nanoparticle suspension was dialyzed against PBS for 6 hours, concentrated using an Amicon® Ultra centrifugal filter device at 2000 rcf, and prepared for storage at −20° C. with 5% w/v sucrose. The resulting lipid nanoparticles were found to have a Z-average particle size of 130.3 nm, and a zeta potential of −5.75 mV. The encapsulation efficiency was 90.8%, as determined by the Ribogreen assay.

Example 7. Preparation of Lipid Nanoparticles Comprising siRNA, Ionizable Lipid MC3, Cholesterol, Phospholipid, PEG-Lipid and 5 Mol % Ganglioside GD3

Ganglioside GD3 was dissolved in methanol. All other lipids were dissolved in ethanol. MC3, Cholesterol, DSPC, PEG2000, and GD3 were mixed with a molar ratio of 49:36.5:8:1.5:5. A Silencer™ GAPDH siRNA (ThermoFisher) was dissolved in 10 mM citrate buffer (pH 3). The volume of the citrate buffer was 9.0 ml, and the volume of the lipid solution was 3.0 ml. The two solutions were loaded into 10 mL Luer-lok syringes which were mounted on a syringe pump, and subsequently introduced to a T-mixer at a flow rate of 8 ml/min for the lipid solution and 24 ml/min for the RNA solution to achieve an N:P ratio of 6:1. After mixing, the nanoparticle suspension was dialyzed against PBS for 6 hours, concentrated using an Amicon® Ultra centrifugal filter device at 2000 ref, and prepared for storage at −20° C. with 5% w/v sucrose. The resulting lipid nanoparticles were found to have a Z-average particle size of 101.9 nm, and a zeta potential of −32.56 mV. The encapsulation efficiency was 92.8%, as determined by the Ribogreen assay.

Example 8. Preparation of Lipid Nanoparticles Comprising siRNA, Ionizable Lipid MC3, Cholesterol, Phospholipid, PEG-Lipid and 10 Mol % Ganglioside GD3

Ganglioside GD3 was dissolved in methanol. All other lipids were dissolved in ethanol. MC3, Cholesterol, DSPC, PEG2000, and GD3 were mixed with a molar ratio of 45:35:8.5:1.5:10. A Silencer™ GAPDH siRNA (ThermoFisher) was dissolved in 10 mM citrate buffer (pH 3). The volume of the citrate buffer was 9.0 ml, and the volume of the lipid solution was 3.0 ml. The two solutions were loaded into 10 mL Luer-lok syringes which were mounted on a syringe pump, and subsequently introduced to a T-mixer at a flow rate of 8 ml/min for the lipid solution and 24 ml/min for the RNA solution to achieve an N:P ratio of 6:1. After mixing, the nanoparticle suspension was dialyzed against PBS for 6 hours, concentrated using an Amicon® Ultra centrifugal filter device at 2000 ref, and prepared for storage at −20° C. with 5% w/v sucrose. The resulting lipid nanoparticles were found to have a Z-average particle size of 119.9 nm, and a zeta potential of −35.68 mV.

Example 9. Preparation of Lipid Nanoparticles Comprising siRNA, Ionizable Lipid MC3, Cholesterol, Phospholipid, and 5 Mol % Ganglioside GD3

Ganglioside GD3 was dissolved in methanol. All other lipids were dissolved in ethanol. MC3, Cholesterol, DSPC, and GD3 were mixed with a molar ratio of 49:37:9:5. A Silencer™ GAPDH siRNA (ThermoFisher) was dissolved in 10 mM citrate buffer (pH 3). The volume of the citrate buffer was 3.0 ml, and the volume of the lipid solution was 1.0 ml. The two solutions were loaded into 5 mL Luer-lok syringes which were mounted on a syringe pump, and subsequently introduced to a T-mixer at a flow rate of 5 ml/min for the lipid solution and 15 ml/min for the RNA solution to achieve an N:P ratio of 6:1. After mixing, the nanoparticle suspension was mixed with 2.5× volume of PBS solution, dialyzed against PBS for 6 hours, concentrated using an Amicon® Ultra centrifugal filter device at 2000 ref, and prepared for storage at −20° C. with 5% w/v sucrose. The resulting lipid nanoparticles were found to have a Z-average particle size of 184.9 nm, and a zeta potential of −32.55 mV. The encapsulation efficiency was 95.0%, as determined by the Ribogreen assay.

Example 10. Preparation of Lipid Nanoparticles Comprising Ionizable Lipid MC3, Cholesterol, Phospholipid, and 5 Mol % Ganglioside GD3

Ganglioside GD3 was dissolved in methanol. All other lipids were dissolved in ethanol. MC3, Cholesterol, DSPC, and GD3 were mixed with a molar ratio of 49:37:9:5. A blank 10 mM citrate buffer (pH 3) was prepared without any RNA dissolved in there. The volume of the citrate buffer was 7.5 ml, and the volume of the lipid solution was 2.5 ml. The two solutions were loaded into 10 mL Luer-lok syringes which were mounted on a syringe pump, and subsequently introduced to a T-mixer at a flow rate of 8 ml/min for the lipid solution and 24 ml/min for the buffer solution. After mixing, the nanoparticle suspension was dialyzed against PBS for 6 hours, concentrated using an Amicon® Ultra centrifugal filter device at 2000 ref, and prepared for storage at −20° C. with 5% w/v sucrose. The resulting lipid nanoparticles were found to have a Z-average particle size of 116.8 nm.

Example 11. Preparation of Lipid Nanoparticles Comprising mRNA, Ionizable Lipid MC3, Cholesterol, Phospholipid, PEG-Lipid, and 3 Mol % Ganglioside GD3

Ganglioside GD3 was dissolved in methanol. All other lipids were dissolved in ethanol. MC3, Cholesterol, DSPC, DMG-PEG2000, and GD3 were mixed with a molar ratio of 49:37.5:9:1.5:3. A GFP-mRNA was dissolved in 10 mM citrate buffer (pH 3). The volume of the citrate buffer was 7.5 ml, and the volume of the lipid solution was 2.5 ml. The two solutions were loaded into 10 mL Luer-lok syringes which were mounted on a syringe pump, and subsequently introduced to a T-mixer at a flow rate of 8 ml/min for the lipid solution and 24 ml/min for the RNA solution to achieve an N:P ratio of 6:1. After mixing, the nanoparticle suspension was dialyzed against PBS for 6 hours, concentrated using an Amicon® Ultra centrifugal filter device at 2000 rcf, and prepared for storage at −20° C. with 5% w/v sucrose. The resulting lipid nanoparticles were found to have a Z-average particle size of 81.5 nm, and a zeta potential of −33.46 mV. The encapsulation efficiency was 92.5%, as determined by the Ribogreen assay.

Example 12. Preparation of Lipid Nanoparticles Comprising mRNA, Ionizable Lipid MC3, Cholesterol, Phospholipid, PEG-Lipid, and 5 Mol % Ganglioside GD3

Ganglioside GD3 was dissolved in methanol. All other lipids were dissolved in ethanol. MC3, Cholesterol, DSPC, DMG-PEG2000, and GD3 were mixed with a molar ratio of 48:36.5:9:1.5:5. A GFP-mRNA was dissolved in 10 mM citrate buffer (pH 3). The volume of the citrate buffer was 7.5 ml, and the volume of the lipid solution was 2.5 ml. The two solutions were loaded into 10 mL Luer-lok syringes which were mounted on a syringe pump, and subsequently introduced to a T-mixer at a flow rate of 8 ml/min for the lipid solution and 24 ml/min for the RNA solution to achieve an N:P ratio of 6:1. After mixing, the nanoparticle suspension was dialyzed against PBS for 6 hours, concentrated using an Amicon® Ultra centrifugal filter device at 2000 ref, and prepared for storage at −20° C. with 5% w/v sucrose. The resulting lipid nanoparticles were found to have a Z-average particle size of 106.9 nm, and a zeta potential of −33.08 mV. The encapsulation efficiency was 92.6%, as determined by the Ribogreen assay.

Example 13. Preparation of Lipid Nanoparticles Comprising mRNA, Ionizable Lipid MC3, Cholesterol, Phospholipid, PEG-Lipid, and 10 Mol % Ganglioside GD3

Ganglioside GD3 was dissolved in methanol. All other lipids were dissolved in ethanol. MC3, Cholesterol, DSPC, DMG-PEG2000, and GD3 were mixed with a molar ratio of 45:35:8.5:1.5:10. A GFP-mRNA was dissolved in 10 mM citrate buffer (pH 3). The volume of the citrate buffer was 7.5 ml, and the volume of the lipid solution was 2.5 ml. The two solutions were loaded into 10 mL Luer-lok syringes which were mounted on a syringe pump, and subsequently introduced to a T-mixer at a flow rate of 8 ml/min for the lipid solution and 24 ml/min for the RNA solution to achieve an N:P ratio of 6:1. After mixing, the nanoparticle suspension was dialyzed against PBS for 6 hours, concentrated using an Amicon® Ultra centrifugal filter device at 2000 ref, and prepared for storage at −20° C. with 5% w/v sucrose. The resulting lipid nanoparticles were found to have a Z-average particle size of 101.5 nm, and a zeta potential of −35.22 mV. The encapsulation efficiency was 85.3%, as determined by the Ribogreen assay.

Example 14. Preparation of Lipid Nanoparticles Comprising mRNA, Ionizable Lipid MC3, Cholesterol, Phospholipid, and 10 Mol % Ganglioside GD3

Ganglioside GD3 was dissolved in methanol. All other lipids were dissolved in ethanol. MC3, Cholesterol, DSPC, and GD3 were mixed with a molar ratio of 46:35:9:10. A GFP-mRNA was dissolved in 10 mM citrate buffer (pH 3). The volume of the citrate buffer was 7.5 ml, and the volume of the lipid solution was 2.5 ml. The two solutions were loaded into 10 mL Luer-lok syringes which were mounted on a syringe pump, and subsequently introduced to a T-mixer at a flow rate of 8 ml/min for the lipid solution and 24 ml/min for the RNA solution to achieve an N:P ratio of 6:1. After mixing, the nanoparticle suspension was mixed with 40 ml PBS solution, stirred for one hour, and subsequently dialyzed against PBS for 6 hours, concentrated using an Amicon® Ultra centrifugal filter device at 2000 rcf, and prepared for storage at −20° C. with 5% w/v sucrose. The resulting lipid nanoparticles were found to have a Z-average particle size of 164.0 nm, and a zeta potential of −50.03 mV. The encapsulation efficiency was 86.0%, as determined by the Ribogreen assay.

Example 15. Preparation of Lipid Nanoparticles Comprising siRNA, Ionizable Lipid SM-102, Cholesterol, Phospholipid, PEG-Lipid, and 5 Mol % Ganglioside GD3

Ganglioside GD3 was dissolved in methanol. All other lipids were dissolved in ethanol. SM-102, Cholesterol, DSPC, DMG-PEG2000, and GD3 were mixed with a molar ratio of 49:36.5:8:1.5:5. An anti-GAPDH siRNA was dissolved in 10 mM citrate buffer (pH 3). The volume of the citrate buffer was 3.0 ml, and the volume of the lipid solution was 1.0 ml. The two solutions were loaded into 5 mL Luer-lok syringes which were mounted on a syringe pump, and subsequently introduced to a T-mixer at a flow rate of 5 ml/min for the lipid solution and 15 ml/min for the RNA solution to achieve an N:P ratio of 6:1. After mixing, the nanoparticle suspension was dialyzed against PBS for 6 hours, concentrated using an Amicon® Ultra centrifugal filter device at 2000 rcf, and prepared for storage at −20° C. with 5% w/v sucrose. The resulting lipid nanoparticles were found to have a Z-average particle size of 74.9 nm, and a zeta potential of −25.12 mV. The encapsulation efficiency was 71.1%, as determined by the Ribogreen assay.

Example 16. Preparation of Lipid Nanoparticles Comprising siRNA, Ionizable Lipid ALC-0315, Cholesterol, Phospholipid, PEG-Lipid, and 5 Mol % Ganglioside GD3

Ganglioside GD3 was dissolved in methanol. All other lipids were dissolved in ethanol. ALC-0315, Cholesterol, DSPC, DMG-PEG2000, and GD3 were mixed with a molar ratio of 49:36.5:8:1.5:5. An anti-GAPDH siRNA was dissolved in 10 mM citrate buffer (pH 3). The volume of the citrate buffer was 3.0 ml, and the volume of the lipid solution was 1.0 ml. The two solutions were loaded into 5 mL Luer-lok syringes which were mounted on a syringe pump, and subsequently introduced to a T-mixer at a flow rate of 5 ml/min for the lipid solution and 15 ml/min for the RNA solution to achieve an N:P ratio of 6:1. After mixing, the nanoparticle suspension was dialyzed against PBS for 6 hours, concentrated using an Amicon® Ultra centrifugal filter device at 2000 ref, and prepared for storage at −20° C. with 5% w/v sucrose. The resulting lipid nanoparticles were found to have a Z-average particle size of 73.6 nm, and a zeta potential of −30.88 mV. The encapsulation efficiency was 35.1%, as determined by the Ribogreen assay.

Example 17. Preparation with Nanoassemblr Ignite of Lipid Nanoparticles Comprising siRNA, Ionizable Lipid MC3, PEG-Lipid, and 5% Ganglioside GD3

Ganglioside GD3 was dissolved in methanol. All other lipids were dissolved in ethanol. MC3, Cholesterol, DSPC, PEG2000, and GD3 were mixed with a molar ratio of 49:36.5:8:1.5:5. A Silencer™ GAPDH siRNA (ThermoFisher) was dissolved in 10 mM citrate buffer (pH 3). The volume of the citrate buffer was 1.5 ml, and the volume of the lipid solution was 0.5 ml. The cargo solution was loaded into a 3 mL Luer-lok syringe and the lipid solution was loaded into a 1 mL Luer-lok syringe which were mounted on a Nanoassemblr Ingite (Precision Nanosystems, Vancouver, Canada). The flow rate was set at 8 ml/min for the lipid solution and 24 ml/min for the RNA solution to achieve an N:P ratio of 6:1. After mixing, the nanoparticle suspension was dialyzed against PBS for 6 hours, concentrated using an Amicon® Ultra centrifugal filter device at 2000 ref, and prepared for storage at −20° C. with 5% w/v sucrose. The resulting lipid nanoparticles were found to have a Z-average particle size of 90.3 nm, and a zeta potential of −25.57 mV.

Example 18. Preparation of Lipid Nanoparticles Comprising a Fluorescently Tagged GFP-mRNA, Ionizable Lipid MC3, Cholesterol, Phospholipid, PEG-Lipid and 3 Mol % Ganglioside GD3

Ganglioside GD3 was dissolved in methanol. All other lipids were dissolved in ethanol. MC3, Cholesterol, DSPC, PEG2000, and GD3 were mixed with a molar ratio of 49:37.5:9:1.5:3. A Cy5 tagged GFP-mRNA (EZ Cap Cy5 EGFP mRNA from APExBIO) was dissolved in 10 mM citrate buffer (pH 3). The volume of the citrate buffer was 7.5 ml, and the volume of the lipid solution was 2.5 ml. The two solutions were loaded into 10 mL Luer-lok syringes which were mounted on a syringe pump, and subsequently introduced to a T-mixer at a flow rate of 8 ml/min for the lipid solution and 24 ml/min for the RNA solution to achieve an N:P ratio of 6:1. After mixing, the nanoparticle suspension was mixed with 20 ml PBS and subsequently dialyzed against PBS for 6 hours, concentrated using an Amicon® Ultra centrifugal filter device at 2000 rcf, and prepared for storage at −20° C. with 5% w/v sucrose. The resulting lipid nanoparticles were found to have a Z-average particle size of 101.0 nm, a PDI of 0.164, and a zeta potential of −23.7 mV. The encapsulation efficiency was 84.9%, as determined by the Ribogreen assay.

Example 19. Preparation of Lipid Nanoparticles Comprising a Fluorescently Tagged GFP-mRNA, Ionizable Lipid MC3, Cholesterol, Phospholipid, and 10 Mol % Ganglioside GD3

Ganglioside GD3 was dissolved in methanol. All other lipids were dissolved in ethanol. MC3, Cholesterol, DSPC, and GD3 were mixed with a molar ratio of 46:35:9:10. A Cy5 tagged GFP-mRNA (EZ Cap Cy5 EGFP mRNA from APExBIO) was dissolved in 10 mM citrate buffer (pH 3). The volume of the citrate buffer was 7.5 ml, and the volume of the lipid solution was 2.5 ml. The two solutions were loaded into 10 mL Luer-lok syringes which were mounted on a syringe pump, and subsequently introduced to a T-mixer at a flow rate of 8 ml/min for the lipid solution and 24 ml/min for the RNA solution to achieve an N:P ratio of 6:1. After mixing, the nanoparticle suspension was mixed with 20 ml PBS and subsequently dialyzed against PBS for 6 hours, concentrated using an Amicon® Ultra centrifugal filter device at 2000 rcf, and prepared for storage at −20° C. with 5% w/v sucrose. The resulting lipid nanoparticles were found to have a Z-average particle size of 226.3 nm, a PDI of 0.251, and a zeta potential of −43.58 mV. The encapsulation efficiency was 95.8%, as determined by the Ribogreen assay.

Example 20. Preparation of Lipid Nanoparticles Comprising an siRNA, Ionizable SS-OP, Cholesterol, Phospholipid, and 10 Mol % Ganglioside GD3

Ganglioside GD3 was dissolved in methanol. All other lipids were dissolved in ethanol. SS-OP (obtained from NOF Corporation), Cholesterol, DSPC, and GD3 were mixed with a molar ratio of 46:35:9:10. A Silencer™ GAPDH siRNA (ThermoFisher) was dissolved in 10 mM citrate buffer (pH 3). The volume of the citrate buffer was 3.0 ml, and the volume of the lipid solution was 1.0 ml. The two solutions were loaded into 5 mL Luer-lok syringes which were mounted on a syringe pump, and subsequently introduced to a T-mixer at a flow rate of 5 ml/min for the lipid solution and 15 ml/min for the RNA solution to achieve an N:P ratio of 6:1. After mixing, the nanoparticle suspension was mixed with 30 ml PBS, concentrated using an Amicon® Ultra centrifugal filter device at 2000 ref, and prepared for storage at −20° C. with 5% w/v sucrose. The resulting lipid nanoparticles were found to have a Z-average particle size of 253.6 nm, a PDI of 0.157, and a zeta potential of −43.59 mV.

Example 21. In Vitro siRNA Knockdown of GAPDH in Primary Human NK Cells, Macrophages, and CD8+ T Cells with LNPs Containing 3% GD3

Lipid nanoparticles comprising a Silencer™ GAPDH siRNA (ThermoFisher), ionizable lipid MC3, cholesterol, phospholipid, PEG-lipid and 3 mol % ganglioside GD3 were prepared as described in Example 6. Prepared lipid nanoparticles were incubated with primary human NK cells, CD8+ T cells, and macrophages at concentrations of 30 nM and 90 nM of siRNA. Samples were collected at 12-hour and 48-hour timepoints, and qPCR analysis of GAPDH gene expression was conducted and data was normalized to ActinB gene expression. Detailed experimental conditions were described as the following:

A. Cell culture
   a. Primary human CD8+ T cell PBC-1041, NK cell PB56C-2, M1 macrophage PBM1C-MON-3
   b. OptiMEM I Reduced serum medium with Pen-Strep
      i. 10 U/mL recombinant human IL-2 for CD8 T cells
      ii. 100 U/mL recombinant human IL-2 and 25 U/ml recombinant human IL-15 for NK cells
      iii. 25 ng/mL recombinant human GM-CSF for macrophages c. Cells seeded at 1×10⁵/mL×100 µL/well (1×10⁴/well) and incubated overnight at 37° C./5% CO2
B. Nanoparticles and control conditions
  a. siRNA alone, untreated, and Lipofectamine+siRNA
  b. standard LNP, GD3 3% LNP, GD3 5% LNP, PEG-less GD3 5% LNP, PSA DOTAP lipoplex
C. Treatments and dosing
  a. Treatment times of 12 h and 48 h
  b. 30 nM and 90 nM siRNA
  c. Prepared NP suspensions at 2× the desired end concentration in media listed above and added 100 uL per well
  d. N=3 experimental replicates, 2 technical replicates
D. qPCR method
  a. GAPDH and ActinB expression levels were measured, using beta-actin as the reference gene to assess GAPDH knockdown
  b. 2 step qPCR method
E. Analysis
  a. Normalized data to siRNA alone treatment
  b. $2^{\wedge}(-\Delta \Delta C_T)$ for relative fold change
F. Results
  a. Table summarizing the average relative fold changes in the GAPDH gene expression in each type of cells.

|  | Timepoint | siRNA Treatment Concentration | Average Relative Fold Change | Standard Deviation | Replicates |
| --- | --- | --- | --- | --- | --- |
| NK Cells | 12 h | 30 nM | 0.688 | 0.063 | 6 |
|  |  | 90 nM | 0.951 | 0.244 | 6 |
|  | 48 h | 30 nM | 0.387 | 0.029 | 6 |
|  |  | 90 nM | 0.319 | 0.044 | 8 |
| Macrophages | 12 h | 30 nM | 0.464 | 0.130 | 6 |
|  |  | 90 nM | 0.436 | 0.134 | 6 |
|  | 48 h | 30 nM | 0.029 | 0.002 | 6 |
|  |  | 90 nM | 0.779 | 0.106 | 6 |
| CD8⁺ T Cell | 12 h | 30 nM | 0.387 | 0.029 | 6 |
|  |  | 90 nM | 0.317 | 0.050 | 6 |
|  | 48 h | 30 nM | 0.550 | 0.208 | 10 |
|  |  | 90 nM | 0.325 | 0.175 | 6 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A lipid nanoparticle composition comprising a ganglioside GD3, an ionizable lipid, phospholipid, cholesterol, and a nucleic acid, said lipid nanoparticle has an average particle size of 30-200 nm ; wherein the lipid nanoparticle does not comprise a PEG-lipid.

2. The lipid nanoparticle composition of claim 1, wherein the phospholipid is DSPC.

3. The lipid nanoparticle composition of claim 1, wherein the ionizable lipid is heptatriaconta-6,9,28,31-tetraen-19-yl 4-(dimethylamino) butanoate.

4. The lipid nanoparticle composition of claim 1, wherein the molar percentage of GD3 out of the total lipid composition is 0.5-20%.

5. The lipid nanoparticle composition of claim 1, wherein the lipid nanoparticles enhance cell transfection and targeting.

6. The lipid nanoparticle composition of claim 5, wherein the cells comprise immune cells and/or tumor cells.

7. The lipid nanoparticle composition of claim 6, wherein the cells are immune cells.

8. The lipid nanoparticle composition of claim 7, wherein the cells are T cells, NK cells and macrophages.

9. The lipid nanoparticle composition of claim 8, wherein the cells are NK cells.

10. The lipid nanoparticle composition of claim 8, wherein the cells are macrophages.

11. The lipid nanoparticle composition of claim 1, wherein the nucleic acid is a DNA, an mRNA, a siRNA, a microRNA, an aptamer, or a gene-editing agent.

12. The lipid nanoparticle composition of claim 11, wherein the gene-editing agent is CRISPR-cas9.

13. A method for administration of a nucleic acid to a subject in need thereof comprising administering to said subject the lipid nanoparticle composition of claim 1.

14. A method for the treatment of a disease or disorder in a subject in need thereof comprising administering to said subject the lipid nanoparticle composition of claim 1.

15. The method of claim 14, wherein the disease is cancer.

16. The method of claim 14, wherein the nucleic acid is an anti-cancer agent or an immunotherapeutic agent.

17. The method of claim 14, wherein the disease is an autoimmune disease.

* * * * *